US00PP30216P2

(12) United States Plant Patent
Ranney

(10) Patent No.: US PP30,216 P2
(45) Date of Patent: Feb. 19, 2019

(54) SMOKEBUSH PLANT NAMED 'NCCO1'

(50) Latin Name: *Cotinus coggygria*
Varietal Denomination: NCCO1

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/731,653

(22) Filed: Jul. 11, 2017

(51) Int. Cl.
*A01H 5/12* (2018.01)

(52) U.S. Cl.
USPC ..... Plt./226

(58) Field of Classification Search
USPC ..... Plt./226

CPC ... A01H 5/02; A01H 5/12; A01H 6/00; A01H 5/00

See application file for complete search history.

(56) References Cited

PUBLICATIONS

American Nurseryman New Plants 2017: Spring Meadow Nursery/ Proven Winners Colorchoice Flowering Shrubs, retrieved on Jun. 12, 2018, retrieved from the Internet at https://www.amerinursery.com/plants/new-plants-2017-spring-meadow-nursery-proven-winners/, (2016) pp. 1-4. (Year: 2016).*

* cited by examiner

*Primary Examiner* — June Hwu
(74) *Attorney, Agent, or Firm* — Cassandra Bright

(57) ABSTRACT

'NCCO1' is a new cultivar of smokebush is disclosed, characterized by a compact habit, dark purple foliage, and large, purple inflorescences. The new variety is a *Cotinus coggygria*, typically produced as an outdoor ornamental plant.

4 Drawing Sheets

Latin name of the genus and species: *Cotinus coggygria*. Variety denomination: 'NCCO1'.

BACKGROUND OF THE INVENTION

The present invention comprises a new and distinct smokebush cultivar hereinafter referred to by the cultivar name 'NCCO1'. This new smokebush was developed through a breeding program at Mills River, N.C. 'NCCO1' was selected from a population of seedlings grown from an open-pollinated, unnamed, *Cotinus coggygria*. The first asexual propagation of 'NCCO1' was carried out in July 2009 by rooting stem cuttings at a research nursery in Mills River, N.C. and has been asexually reproduced repeatedly by vegetative cuttings and tissue culture over a 8 year period. 'NCCO1' roots from softwood cuttings treated with a basal dip of 6,000-8,000 ppm indole butyric acid (potassium salt) in water. 'NCCO1' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Compact habit.
2. Dark purple foliage.
3. Large, purple inflorescences.

COMPARISON WITH PARENT VARIETY

Plants of the new variety are similar to plants of the parent in most horticultural characteristics. 'NCCO1' differs however, in the following:

1. More compact plant habit than the parent.
2. Larger inflorescence than the parent.
3. Darker purple foliage than the parent.

COMPARISON WITH COMMERCIAL CULTIVAR

'NCCO1' is distinguished from the commercial cultivar *Cotinus coggygria* 'Velvet Cloak', unpatented in that 'NCCO1' has a more compact habit and will grow to be 2 meters tall by 2 meters wide with moderate pruning. *C. coggygria* 'Velvet Cloak' will grow to be taller than 3 meters with similar pruning. 'NCCO1' has dark Greyed-Purple (N186A) mature foliage and darker Greyed-Purple (187A) inflorescence panicles compared to *C. coggygria* 'Velvet Cloak' with Greyed-Purple (N186D) foliage and lighter-colored Greyed-Purple (183B) inflorescence panicles.

BRIEF DESCRIPTION OF THE DRAWINGS

This new smokebush is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new smokebush.

DETAILED BOTANICAL DESCRIPTION

Figure 1:
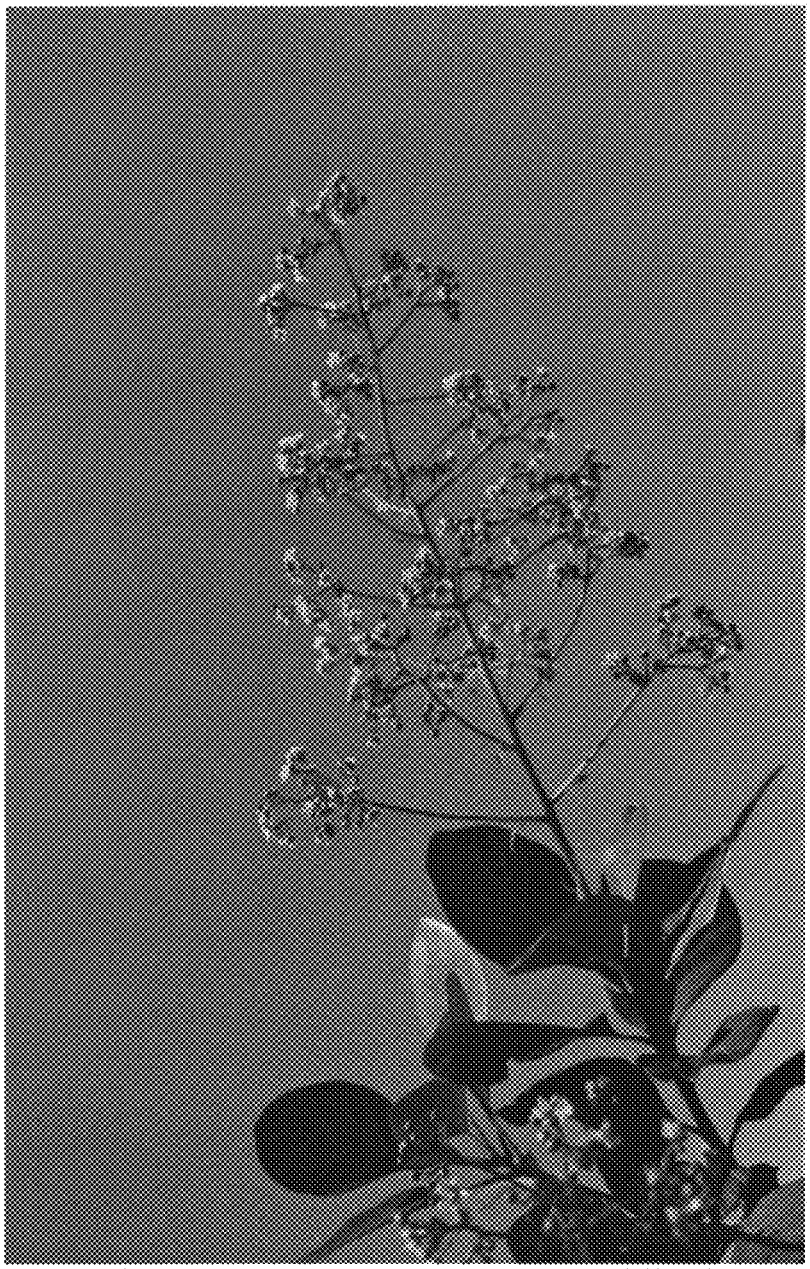
FIG. 1 is a color photograph showing the inflorescence and flowers of 'NCCO1' in spring 2017 on an eight-year-old tree.
Figure 2:
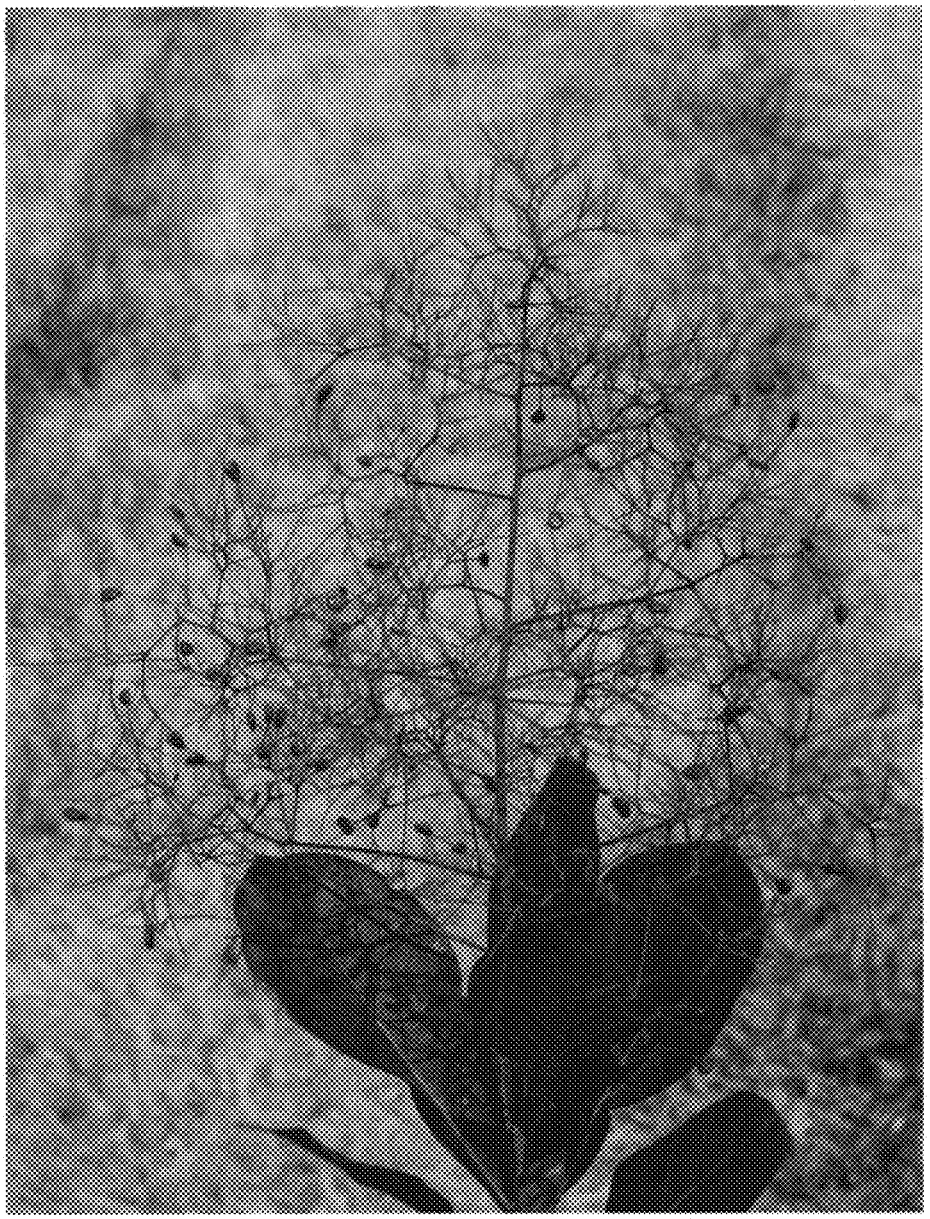
FIG. 2 is a color photograph showing the inflorescence and seeds of 'NCCO1' in summer 2016 on a seven-year-old tree.
Figure 3:
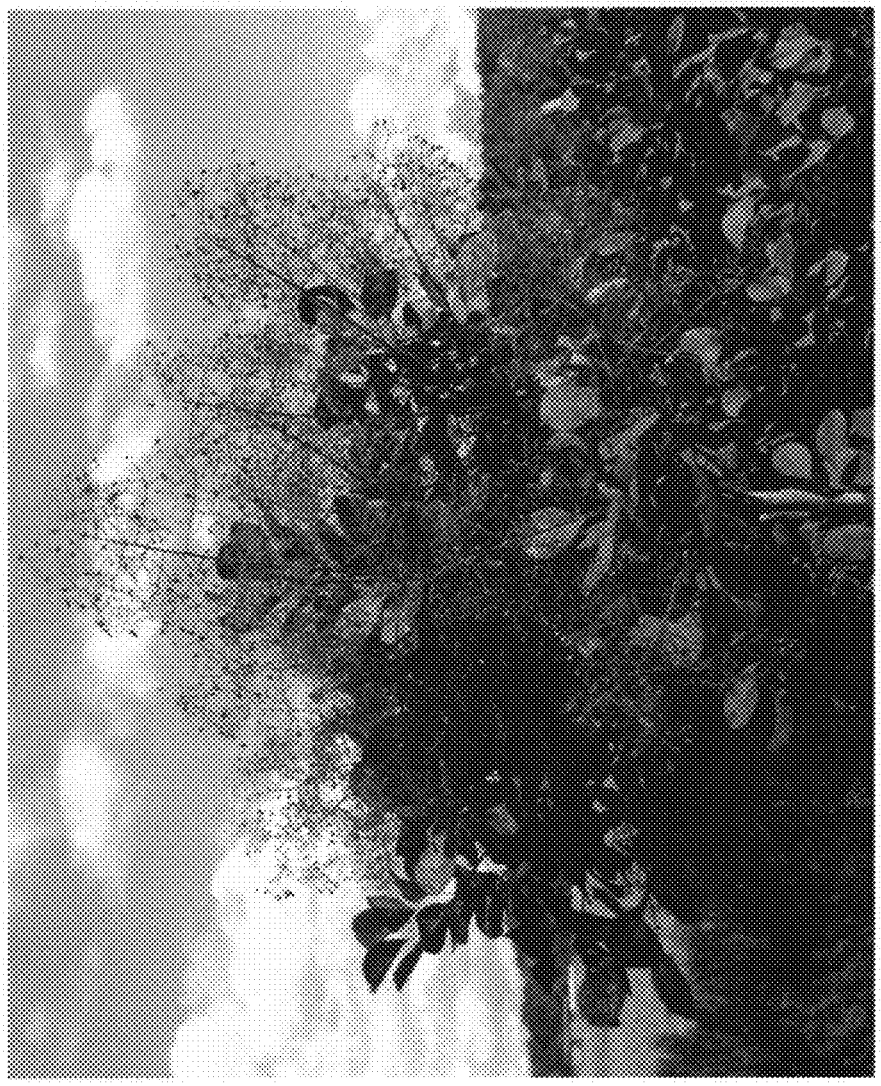
FIG. 3 is a color photograph showing inflorescences and foliage of 'NCCO1' in summer 2016 on a seven-year-old tree.
Figure 4:
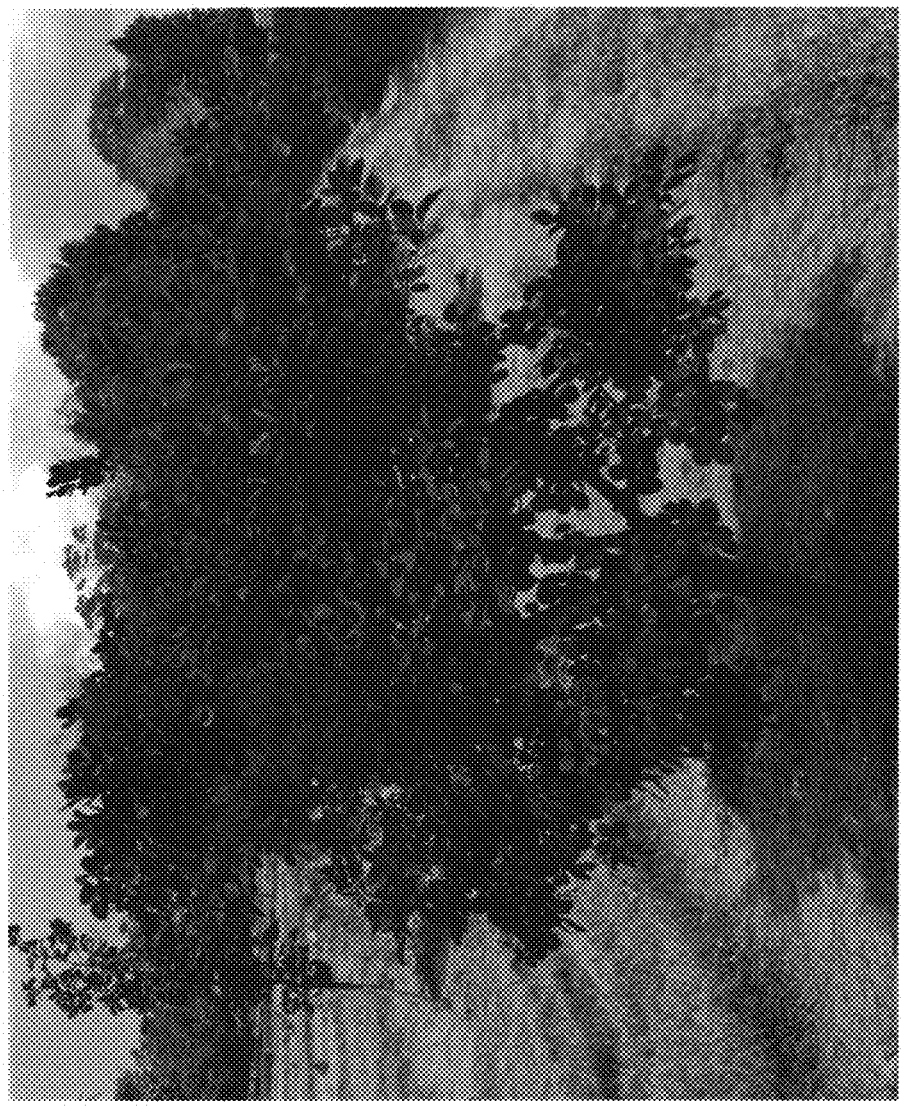
FIG. 4 is a color photograph showing the form of 'NCCO1' in summer 2016 on a seven-year-old tree.

The following is a detailed description of the botanical characteristics of the new and distinct smokebush variety plant known by the denomination 'NCCO1'. The detailed description was taken on a six-year-old field-grown plant in Mills River, N.C. in 2015. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name*.—*Cotinus coggygria* 'NCCO1'.

*Common name*.—Smokebush.

Parentage: Seedling grown from an open-pollinated *Cotinus coggygria.*

Plant description:

*Growth habit*.—Upright shrub.

*Height*.—Approximately 2 m at 6 years.

*Width*.—Approximately 1.5 m at 6 years.

Shoot and stem:

*Shoot color* (*current year*).—Greyed-Purple (187B) flush over Greyed-Green (198A) with mottled spots of Grey-Brown (N199A).

*Shoot texture* (*current year*).—Spotted with Grey-Brown (N199D) lenticels.

*Shoot diameter* (*current year*).—4 mm (typically ranging from 3 mm-5 mm) at base.

*Annual shoot length*.—Avg. 10 cm (typically ranging from 6 cm to 14 cm).

*Internode length*.—Avg. 1 cm (typically ranging from 0.5 cm to 2.0 cm.

*Lateral branch length*.—Average 63.4 cm (typically ranging from 48.0 to 90.0 cm).

*Lateral branch diameter*.—Avg. 0.8 cm (typically ranging from 0.3 to 1.3 cm).

*Lateral branch texture*.—Spotted with Greyed-Green (197D) lenticels.

*Stem/trunk diameter* (10 *cm from base*).—10 cm.

*Stem/trunk color*.—Greenish-Grey (202D) to Brownish-Grey (N200B).

Leaves:

*Type*.—Simple.

*Persistence*.—Deciduous.

*Arrangement*.—Alternate.

*Shape*.—Obovate.

*Apex*.—Obtuse to obcordate.

*Base*.—Cuneate.

*Margins*.—Entire, slightly undulate.

*Venation*.—Reticulate.

*Vein texture*.—Glabrous.

*Emerging leaves*.—Color: Upper: Greyed-Purple (187A) to Dark Purplish-Grey (N187A). Lower: Greyish-Purple (N187B). Vein color: Moderate-Red (185B), both sides. Texture: Glabrous, upper and lower surfaces.

*Mature leaves during growing season*.—Length of lamina: Avg. 5.2 cm (typically ranging from 3.1 to 7.5 cm). Width: Avg. 3.9 cm (typically ranging from 3.1 to 5.8 cm). Color: Upper: Greyed-Purple (N186A). Lower: Greyed-Purple (N187A). Vein color: Ranging from Red-Purple (61B) to Greyed-Purple (N187A), both sides.

*Fall color*.—Upper: Combination of Greyed-Orange 169B, Red 46C and Greyed-Orange N163B. Lower: Combination of Greyed-Orange 169B, Red 46C and Greyed-Orange N163B. Vein color: Ranging from Greyed-Orange 169B and Greyed-Orange N163B), both surfaces. Texture: Glabrous.

*Leaf attachment*.—Petiolate.

*Petiole*.—Length: Avg. 2.9 cm (typically ranging from 1.3 to 4.0 cm). Diameter: About 0.1 cm. Color: Greyed-Purple (183B). Texture: Glabrous.

Inflorescence:

*Flower arrangement*.—Terminal panicle.

*Inflorescence type*.—Panicle or thryse.

*Inflorescence length/height*.—Avg. 17.4 cm (typically ranging from 12.0 to 20.5 cm).

*Inflorescence width*.—Avg. 15.5 cm (typically ranging from 13.0 to 17.0 cm).

*Inflorescence aspect*.—Upward and outward.

*Individual flowers per panicle*.—Approximately 300.

*Flowering season*.—Spring; May in Mills River, N.C.

*Lastingness*.—Flowering begins first week of June in Michigan. flowerless panicles persist until early August.

*Flower bud*.—Shape: Oblong. Length: About 0.15 cm. Width: About 0.10 cm. Color: Closest to Greyed-Purple (187A).

*Flower*.—Shape: Rotate. Height: About 0.2 cm. Width: About 0.5 cm.

*Petal*.—Arrangement: Rotate. Number: 5. Fused: Not fused. Shape: Ovate. Margin: Entire. Apex: Acute. Base: Cuneate. Length: About 0.2 cm. Width: About 0.15 cm. Color: Closest to Yellow-Green (150C). Texture: Glabrous.

*Calyx*.—Shape: Campanulate. Length: About 0.1 cm. Diameter: About 0.3 cm.

*Sepal*.—Arrangement: Rotate. Number: 5. Shape: Ovate. Margin: Entire. Apex: Acute. Base: Cuneate. Length: About 0.1 cm. Width: About 0.1 cm. Color: Closest to Yellow-Green (144C). Texture: Glabrous.

*Peduncle*.—Length: Avg. 17.4 cm (typically ranging from 12.0 to 20.5 cm). Diameter: Avg. 0.2 cm (typically ranging from 0.1 to 0.2 cm). Color: Greyed-Purple (187A). Texture: Glabrous.

*Pedicels*.—Flowered pedicel: Length: Avg. 0.6 cm (typically ranging from 0.1 to 1.2 cm). Width: Less than 0.1 cm. Color: Greyed-Purple (187A). Texture: Pubescent. Flowerless pedicel: Length: Avg. 0.8 cm (typically ranging from 0.3 to 1.7 cm). Width: Less than 0.1 cm. Color: Greyed-Purple (187A). Texture:

Densely pubescent. Hairs approximately 1 mm, colored near Greyed-Purple 183A.

Reproductive organs:

*Gynoecium*.—Pistil number: 1. Pistil length: About 0.02 cm. Stigma shape: Club-shaped. Stigma color: Yellow-Green (144B). Style length: About 0.01 cm. Style color: Yellow-Green (144B). Ovary color: Yellow-Green (144B).

*Androecium*.—Stamen number: 5. Anther shape: Kidney-shaped. Anther length: About 0.03 cm. Anther color: Yellow-Orange (15A). Filament length: About 0.1 cm. Amount of pollen: Low. Pollen color: Yellow-Orange (15A).

Fruit and seed:

*Fruit type*.—Drupe.

*Fruit length*.—About 0.3 cm.

*Fruit diameter*.—About 0.5 cm.

*Fruit color*.—Greyed-Purple (N186A).

*Fruit texture*.—Glabrous.

*Seed number*.—1 seed per fruit.

*Seed length*.—About 0.3 cm.

*Seed diameter*.—About 0.5 cm.

*Seed color*.—Grey-Brown (199C).

Disease and insect resistance: No significant disease or insect pests have been observed.

Cold hardiness: At least USDA zone 6b; testing has not been completed in colder zones.

What is claimed is:

1. A new and distinct smokebush plant named 'NCCO1' as illustrated and described herein.

* * * * *